United States Patent [19]

Racioppi et al.

[11] Patent Number: 5,545,555
[45] Date of Patent: Aug. 13, 1996

[54] MICROBIAL TRANSPORT MEDIA

[75] Inventors: Stephen G. Racioppi, Norcross, Ga.; James P. Brinker, Dudley, Mass.

[73] Assignee: Microtest, Inc., Snellville, Ga.

[21] Appl. No.: 279,589

[22] Filed: Jul. 25, 1994

[51] Int. Cl.$^6$ ............... C12N 1/20; C12N 1/12; C12N 1/00

[52] U.S. Cl. .................. 435/253.6; 435/252.1; 435/243

[58] Field of Search ............ 435/240.1, 252.1, 435/243, 235.1, 240.31, 240.3, 240.54, 240.4, 240.2, 253.6

[56] References Cited

U.S. PATENT DOCUMENTS

| | | | |
|---|---|---|---|
| 4,375,510 | 3/1983 | Jordan | 435/34 |
| 4,529,702 | 7/1985 | Bryan | 435/253 |
| 5,108,927 | 4/1992 | Dorn | 435/296 |
| 5,110,722 | 5/1992 | Brockbank et al. | 435/1 |
| 5,232,848 | 8/1993 | Wolfe et al. | 435/240.31 |
| 5,354,663 | 10/1994 | Charm et al. | 435/32 |
| 5,474,931 | 12/1995 | DiSorbo et al. | 435/240.31 |

OTHER PUBLICATIONS

Saiki, Randall K. (1989) "The Design and Optimization of the PCR" PCR Technology, pp. 7–16. Stockton Press, U.K.
Stuart, R. D. et al. (1954) "The Problem of Transport of Specimens for Culture of Gonococci" Can. J. Public Health 45:73–83.
Amies, C. R. et al. (1967) "A modified Formula for the Preparation of Stuart's Transport Medium" Can. J. Public Health 58:296–300.
Bailey et al. (1978) "Specimen containers and their transport" Diagnostic Microbiology, pp. 29–32. From *Diagnostic Microbiology*, The C. V. Mosby Company.
Bowie, W. R., K. K. Holmes (1977) "Nongonococcal Urethritis" Infectious Diseases, pp. 486–487. Harper & Row, Publishers. 2nd ed.
ATCC Catalogue of Bacteria and Bacteriophages, 17th ed., 1989, pp. 348–350.
Sigma 1992 Catalogue—Cell Culture Reagents, pp. 56–63, 35–46, 83–99.
The Merck Index, 11th ed., Merck & Co., The Rahway, N.J., 1989, pp. 93, 387, 735, 1151, 1561.

*Primary Examiner*—Irene Marx
*Assistant Examiner*—Kristin Larson
*Attorney, Agent, or Firm*—Saliwanchik & Saliwanchik

[57] ABSTRACT

A microbial transport medium for the collection, transport and storage of samples suspected of having Chlamydia, Mycoplasma, Ureaplasma or viral pathogens comprises a balanced salt solution, a proteinaceous stabilizer, and carbohydrate and amino acid nutrient sources. The medium is buffered to maintain physiological pH and includes a pH indicator in order to maintain pH fluctuation. The medium further comprises antimicrobial and antifungal agents and can comprise gelatin. Samples can be stored in the medium at temperatures ranging from room temperature to minus 70° C. Additionally, the transport medium can be used in standardized commercial ELISA and PCR assays.

2 Claims, No Drawings

MICROBIAL TRANSPORT MEDIA

BACKGROUND OF THE INVENTION

The collecting and processing of clinical samples is an important aspect in the identification of specific causative agents of disease in the diagnostic process. General considerations in collecting biological samples for examination and culture include the minimization of external contamination of the sample. Once the sample has been collected, the handling and transport of that sample to the clinical laboratory is also an important aspect of the diagnostic process. All samples, regardless of their type and content, are preferably kept hydrated. Further, oxidative processes and enzymatic destruction of the pathogens within the sample should be prevented.

A variety of general and specialized transport media have been devised for the collection, delivery and delayed processing of clinical samples. See, for example, Amies, Can. J. Public Health, 58:296–300 (1967); Bailey et al., "Specimen Containers and their Transport," 29–32, in Diagnostic Microbiology, The C. V. Mosby Co., St. Louis, Mo. (1978); U.S. Pat. No. 4,529,702. However, it is known that different organisms can have particular requirements in order to retain viability in a collection or transport medium. Certain of these organisms, many of which are clinically significant due to their pathogenicity or resistance to treatments, can present difficulties in retaining viability using a single collection or transport media. Examples of some of these organisms are discussed below.

Chlamydia are non-motile, Gram-negative, obligate intracellular parasites. These microbes have been identified as the causative agents of psittacosis-ornithosis, lympho-granuloma venereum, and trachoma and inclusion conjunctivitis in humans. *Chlamydia trachomatis* has also been implicated in a pneumonia-type syndrome in infants. Chlamydia has further been identified as the agent most frequently involved in non-specific or nongonococcal urethritis. In studies conducted in England and the United States, *Chlamydia trachomatis* was isolated from between 30% and 50% of patients with nonspecific urethritis. Bowie and Holmes (1977) in *Infectious Diseases*, 2nd Ed. (Hoeprich, Paul D., ed.), Harper & Row, Hagerstown, pp. 486–487.

Chlamydia must be grown within a cell and can be cultivated in tissue culture or in the yolk sac of an embryonated egg. Clinical specimens suspected of having the Chlamydia pathogen must therefore be collected in a manner so as to minimize external bacterial contamination that would hinder cell culture growth. Samples suspected of containing Chlamydia are typically stored at –70° C.

Mycoplasmas, which include the genera Mycoplasma and Ureaplasma, are extremely small, free-living bacteria which lack a cell wall. Mycoplasmas are therefore resistant to conventional antimicrobials which act upon the bacterial cell wall, such as penicillin and penicillin derivatives. Organisms classified in the genus Mycoplasma do not hydrolyze urea. The organisms in the genus Ureaplasma include those that hydrolyze urea. Both genera have been implicated as agents in diseases of humans. For example, *M. pneumoniae* has been reported to cause approximately 20% of the cases of primary atypical pneumonia and bronchitis. Ureaplasma have been associated with nongonococcal urethritis. Other diseases and illnesses suggested to be linked to mycoplasmal infections include rheumatoid arthritis and neurological disorders.

Growth media specific for mycoplasma often include a pH indicator for the identification of acid production and various antimicrobials to destroy hardy commensals and prevent overgrowth of the sample. A transport medium that has been used satisfactorily for swab clinical specimens of mycoplasmas comprises trypticase soy broth with 0.5% bovine albumin (Bailey, supra).

Viral pathogens are many and diverse. A common feature of most viruses however, is that they are preferably grown and propagated in cell culture. Therefore, the collection and handling of clinical specimens is extremely important. Specimens must be collected so as to, inter alia, minimize the possibility of bacterial contamination of the cell cultures.

It is clear that the use of a collection or transport medium that may be optimal for use with one type of organism may not be optimal for use with all of these organisms. A sample suspected of having present one or more of the above pathogenic organisms can therefore require the collection of more than one sample using previously available media. It is therefore desirable to have a single collection or transport medium which can sustain viability of a plurality of organisms. One example of a general support media for a variety of microbial pathogens within a variety of clinical samples is Stuart's medium. Stuart's medium (Stuart et al., supra) is a well-known buffered transport medium which includes the components glycerophosphate to permit minimal multiplication and sodium thioglycollate as a reducing agent to prevent oxidation within the sample. Stuart's medium contains no nutrients. The absence of nutrients retards the growth of commensal organisms within the sample which can multiply and overgrow the less hardy pathogens. However, the absence of nutrients in Stuart's media can be detrimental to the viability of less hardy pathogens.

The presence or suspected presence of fastidious pathogens e.g., mycoplasmas, Chlamydia, or certain viruses, in a clinical sample can require that special care be taken with that sample. Specialized media are known which support the viability of a variety of fastidious pathogens. However, these known media were not able to be used successfully with a wide variety of diagnostic procedures, e.g., membrane enzyme-linked immunosorbent assay (membrane ELISA) or polymerase chain reaction (PCR). A collection or transport media which is compatible with reagents or can be used as a reagent itself in the diagnostic procedures performed on the sample can provide an advantage in the field of microorganism diagnosis. Membrane ELISA utilizes a porous membrane to allow certain particles of a particular size to pass through the membrane enhancing the ability of reactants to come into contact, e.g., the antigen and antibody in the formation of the antigen/antibody complex.

Polymerase chain reaction (PCR) is becoming a valuable technique for organism identification in the clinical and reference laboratory and can require specialized reagents for its successful application to microbial diagnostics. Saikki, R. K. (1989) in *PCR Technology*, Stockton Press, United Kingdom pp. 7–16. PCR is a process by which selected pieces of DNA are amplified within a sample through the action of the enzyme, DNA polymerase so that organisms can be selectively and specifically identified even when they are present in extremely small amounts. In a clinical diagnostic procedure, primers to a single identifying fragment or sequence of patbogen DNA can be added directly to a clinical sample. If the suspected pathogen is present in the sample, PCR techniques can be used to amplify the patbogen DNA so that it is then easily detectable and its presence confirmed. PCR thus allows a sample to be tested directly for the presence of pathogens without requiring that the pathogen be isolated from the clinical sample and cultured separately before positive identification.

A single medium which can be used in the collection of a clinical sample, transport of the sample, and in the diagnostic procedure, e.g. ELISA or PCR, is therefore an advantageous tool in the collecting and processing of clinical samples. The advantages include not only convenience for the clinician or diagnostician, but can provide an economic benefit in the reduction of redundant sample collection and performance of a plurality of identification procedures.

BRIEF DESCRIPTION OF THE INVENTION

The invention concerns a novel universal medium which can be useful for the collection, transport and storage of clinical samples suspected of having a variety of pathogens, including the fastidious pathogens Chlamydia, Mycoplasma, Ureaplasma or vital pathogens and wherein the medium is further compatible with the detection procedures and methodologies. For purposes of the subject invention, a universal medium refers to a medium in which viability for a plurality of organisms can be sustained. The subject transport medium comprises an aqueous balanced salt solution buffered at approximately physiological pH, at least one protein stabilizer, and carbohydrate and amino acid nutrient sources. The composition also comprises an antimicrobial component and an indicator of pH.

The subject invention also concerns an article of manufacture which provides specific directions for use with ELISA, PCR, or other identification techniques. Novel methods of use relating to these novel compositions and articles of manufacture, and kits comprising same, are also provided by the subject invention.

One object of the invention is to provide a single transport medium which can sustain the viability of the suspect organisms in a clinical sample and which can be used as a reagent, or is compatible with other reagents employed, in standard detection methods. The detection methods of interest include, inter alia, standard microbial assays, enzyme-linked immunosorbant assay (ELISA), and PCR. A particular advantage of the subject invention is its successful and direct use with, or applicability to membrane ELISA and commercial PCR assays.

It is a further object of the subject invention to provide a transport medium which can support the viability of fastidious organisms and minimize the risk of contamination resulting from overgrowth by commensal organisms. In a preferred embodiment, the subject invention can comprise a composition which has a specific viscosity. In another embodiment of the subject invention, the buffer salts can include a phosphate component. However, the subject invention is unique in that in one embodiment comprising phosphate, only a single monophosphate component is used.

It is still another object of the subject invention to provide a method for using the novel transport medium to collect and transport the clinical sample and to use the medium as a reagent, or where the medium is compatible with other reagents used with detection or diagnostic procedures.

Thus, the advantages provided by the subject universal transport medium include:

1. utilization of the subject universal transport media for more than one type of test and for more than one type or organism (e.g., viruses, Chlamydia, mycoplasmas);

2. rejection of fewer diagnostic tests due to improper transport media;

3. reduction of costs to the laboratory because providing multiple types of transport media becomes unnecessary;

4. minimization of physician education or training concerning the appropriate transport medium to use for the desired test;

5. performance of confirmatory tests on the same sample; and 6. other or additional tests can be subsequently requested after the sample has already been collected and/or reached the laboratory.

DETAILED DESCRIPTION OF THE INVENTION

The subject invention concerns microbial collection or transport media for the collection, storage and delivery of clinical samples suspected of harboring fastidious microorganisms, including Chlamydia, Mycoplasma, Ureaplasma or viral pathogens. The subject transport media supports the viability of these fastidious pathogens while hindering the growth of the more hardy normal flora which can be present in the sample and potentially contaminate the sample rendering it incapable of yielding a positive identification of those pathogens.

More specifically, the transport medium of the subject invention comprises, in an aqueous solution: carbohydrate in the form of sugar, e.g., the complex sugar, sucrose; buffer salts, including HEPES, sodium, calcium, and magnesium salts; an amino acid nutrient source; a pH indicator; a proteinaceous stabilizing agent; and antimicrobial compositions, which can include vancomycin, colistin, or amphotericin. A separate viscosity stabilizer can also be included.

The preferred composition includes as a stabilizing component, bovine serum albumin (BSA) rather than whole bovine serum, as is used in many currently available media. BSA has the added advantage that it does not inhibit attachment and growth of myxo and paramyxoviruses.

A preferred embodiment of the subject invention has, in an aqueous solution of about 1.0 liter (total volume) the following composition:

| | |
|---|---|
| sucrose | 65–75 g |
| HEPES | 5–7 g |
| KCl | 4–6 g |
| L-glutamic acid | 0.5–1.0 g |
| phenol red | 0.25–1.0 ml |
| NaOH | 1.0–2.0 ml |
| CaCl$_2$ | 0.1–0.5 g |
| MgSO$_4$.7H$_2$O | 0.1–0.3 g |
| bovine serum albumin | 1.0–20.0 g |
| vancomycin | 0.01–0.05 g |
| colistin | 0.1–0.3 g |
| amphotericin | 2.0–3.0 ml |

The particular preferred embodiment includes, in 995.4 ml of H$_2$O: sucrose—68.46 g; HEPES-5.96 g; Na$_2$HPO$_4$-0.122 g; KCl-4.72 g; L-glutamic acid-0.72 g; phenol red-0.52 ml; NaOH-1.44 ml; CaCl$_2$-0.27 g; MgSO$_4$.7H$_2$O-0.20 g; BSA- 5.0 g; gelatin-5.0 g; vancomycin—0.02 g; colistin-0.19 g; amphotericin-2.40 ml. This composition is hereinafter referred to as Transport Medium A.

The medium of the subject invention has relatively low viscosity and can be used in a variety of laboratory procedures. The preferred embodiment can comprise an aqueous solution of the above component where the viscosity measures a Bloom value less than 125. A preferred Bloom value is less than 100, more preferably between 40–100 and most preferably about 60. "Bloom value" is the standard measure of viscosity and is well known in the art. One example of a component which can provide the desired viscosity is gelatin, which is commercially available. Sigma Chemical Co., St. Louis Mo. In the preferred embodiment, to obtain a final product having a Bloom value less than 125, 0–10 grams of gelatin per about 1 liter of solution can be added. Gelatin can also advantageously impart a cryoprotectant property to the transport medium. Gelatin further supplements the stabilizing effect of BSA for extended storage of the clinical sample and therefore can permit the reduction of BSA amounts in embodiments where gelatin is present. In an embodiment where gelatin is absent, BSA is typically provided at about two times the normal amount. The embodiment having no gelatin or phosphate, and about 10 grams of BSA per liter of medium is referred to as Transport Medium B. Transport Medium C is identical to Transport Medium A, except the gelatin used for Transport Medium C has a significantly higher Bloom value.

Dimethyl sulfoxide (DMSO) and sorbitol are typically used as cryoprotectants. However, these components can be toxic to living cells at certain levels or upon prolonged storage at ambient temperatures. Use of the subject transport media advantageously ensures viability of pathogens within a sample that is frozen then thawed, but has no toxic effects as associated with DMSO or sorbitol.

It should be understood by persons of ordinary skill in the art that the subject invention can also include equivalent components. For example, the carbohydrate nutrient source can include other complex sugars as well as simple sugars, including glucose, fructose, and the like. In addition, other L-amino acids can be used instead of L-glutamic acid.

It would also be within the capability of those with ordinary skill in the art to include other salts which function in substantially the same way as those listed in the preferred embodiment. For example, in one embodiment of the subject invention, the medium can comprise a phosphate salt as a buffer or pH stabilizer. In a preferred embodiment which comprises phosphate buffer, sodium phosphate monobasic ($NaH_2PO_4$) can be added to the solution at approximately 0.1 to 0.15 grams per liter, and preferably about 0.12 grams.

Vancomycin, amphotericin and colistin are antimicrobial agents that inhibit growth of the normal flora within a clinical sample. Vancomycin is a narrow spectrum antibiotic which inhibits cell wall synthesis and therefor inhibits Gram-positive microbes such as Staphylococcus and Clostridia. It would be understood by persons of ordinary skill in the art that other narrow spectrum antibiotics effective in inhibiting cell wall synthesis in Gram-positive bacteria can also be used.

Amphotericin is a broad spectrum antifungal and antiprotozoan agent that interacts with the sterols of the cell membrane. It would also be understood by ordinarily skilled artisans that other agents which have, either singularly or separately, antifungal or antiprotozoal activity can also be used in the subject medium.

Colistin is a narrow spectrum antimicrobial effective on Gram-negative enterics. Substitution of other narrow spectrum antibiotics effective against Gram-negative enterics would also be readily recognized in the art. The inclusion of these antimicrobial agents in the medium of the subject invention prevent the overgrowth by the hardy normal flora in the specimen having Chlamydia, Mycoplasma, Ureaplasma or a virus which can be difficult to grow in culture.

In a preferred embodiment, the medium is adjusted to approximately physiological pH. A particularly preferred embodiment comprises a medium which is adjusted to a pH of 7.3±0.2. The subject medium is isotonic and non-toxic to mammalian cells. For example, the medium is particularly advantageous in that it is compatible with use in commercial ELISA (including membrane ELISA), PCR or DNA probe assays.

In practice, the subject transport media can be provided in 1 dram vials for convenient inoculation, or can be provided in a standard 15 ml Sarstedt polypropylene centrifuge tube, containing a premeasured 3 ml volume of medium. It would be understood that other biologically inert materials can also be used for the container tubes. Also, the volumes and sizes used herein are easily and readily adaptable to other situations. Also within the centrifuge tube along with the medium can be included glass beads. Typically, four (3 mm) glass beads can be included. This size of glass bead is preferred in order to prevent them from becoming trapped in the bottom of the centrifuge tube while being vortexed.

The novel media of the subject invention, as stated above, are advantageously useful with certain diagnostic procedures, including ELISA (especially membrane ELISA), PCR, and DNA probe techniques. Thus, the subject invention includes novel methods of using a transport medium where a single medium can be employed for collection, storage, transport, or analysis of a sample. The subject method of collecting and transporting the sample, which would be readily recognized by, persons of ordinary skill in the art includes the steps of collecting the sample by standard procedures, and inoculating the medium with the sample according to known techniques.

A further advantage of the subject invention results from the subject medium's compatibility with analysis procedures which can be performed on the sample to detect a particular fastidious organism and thereby diagnose an infection with such an organism in a patient. A particularly useful aspect of the subject medium, e.g., Transport Medium A, is the novel method of using the medium to collect, transport, and analyze the sample for detecting or diagnosing a vital, chlamydial, mycoplasmal, or ureaplasmal infection by membrane ELISA methods. Another novel method of use employs the subject media in PCR techniques for the detection and diagnosis of those organisms. The subject media also provide a novel method of using nucleic acid probe techniques e.g., DNA probes. The subject media inoculated with the test sample can be used directly with the reagents employed in these analysis procedures, effectively becoming a reagent in the procedure. The subject media does not interfere with the other standard reagents used in these procedures. This is advantageous in that the transport medium does not have to be completely removed from the sample, e.g., cells, prior to conducting these ELISA, PCR or nucleic acid probe procedures.

By incorporating a label indicating specific instructions for using the novel media with ELISA, PCR or nucleic acid probe techniques with the tubes containing media and glass beads, the subject invention includes a novel article of manufacture.

Kits can also be provided where the novel medium is provided and is separately packaged with other materials useful for collection, transport, and analysis of a sample. For example, in a preferred embodiment, the kit comprises the novel medium (3 ml) provided with four 3 mm glass beads in a 15 ml polypropylene centrifuge tube, pre-scored swabs for collection of the sample and inoculation in the medium, and a patient information card, in a leak-resistant compartmentalized package. A typical compartmentalized package for the subject kit can be a polypropylene bag, preferably having two pockets for convenience of use.

Following are examples which illustrate procedures, including the best mode, for practicing the invention. These examples should not be construed as limiting. All percentages are by weight and all solvent mixture proportions are by volume unless otherwise noted.

EXAMPLE 1

Preparation and Quality Control of Transport Medium A

To prepare a 25 liter batch of Transport Medium A, the following components provided in amount as shown in Table 1, below.

TABLE 1

Transport Medium A

| Component | Amount of Component |
| --- | --- |
| $H_2O$ | 24.89 liters |
| sucrose | 1711.43 g |
| HEPES | 148.99 g |
| $NaH_2PO_4$ | 3.05 g |
| KCl | 10.0 g |
| L-glutamic acid | 18.0 g |
| phenol red | 13.0 ml |
| gelatin | 125 g |
| NaOH | 36.0 ml |
| $CaCl_2$ | 6.63 g |
| $MgSO_4 \cdot 7H_2O$ | 5.0 g |
| BSA | 250 g |
| vancomycin | 0.62 g |
| colistin | 0.35 g |
| amphotericin | 60.0 ml |

In the amounts shown in Table 1, HEPES, KCl, L-glutamic acid, phenol red, and sodium hydroxide initially dissolved in 1667 ml of water and added to 18.89 liters of water. Calcium chloride (66.63 g) is dissolved in 833 ml of water and added to the initial solution. 5 g of $MgSO_4 \cdot 7H_2O$ are dissolved in 834 ml of water and added to the solution. 125 g of BSA and 125 g of gelatin are dissolved in 1667 ml of water and added to the solution. The antimicrobial components, as shown in Table 1 are dissolved in 1 liter of water and added to the solution to yield the final product, Transport Medium A.

Each lot of the subject transport medium is tested for quality control in the following manner:

Appearance: Each lot should be orange-red (when frozen) and red in color at refrigerated or room temperature. The media should be almost clear with a small amount of turbidity. Lots that are yellow, purple or turbid are rejected.

Toxicity: A 0.3 ml aliquot of medium is inoculated into each of 2 MRC-5 shell vials. The vials are incubated for 18 hours at 37° C. The result is recorded as normal or abnormal.

Acceptable pH Range: 7.1–7.5

Microbial Contamination Check: 55 tubes or 1% of each lot are randomly selected for bioburden testing. Sets of 10 tubes are placed in racks which contain 20 tryptic soy broth (TSB) tubes. One 2 ml and one 0.5 ml TSB tube is pipetted into a 0.5 ml TSB tube. After all pipetting is done, 3 racks are placed in a 37 degree C. incubator with ambient atmosphere and 2 racks are placed in a 37 degree incubator with ambient atmosphere and 2 racks are placed in a 37 degree incubator with a 5% $CO_2$ atmosphere.

After a 72 hour incubation, the racks are removed from the incubators and examined for visible turbidity. Tubes showing turbidity are plated onto chocolate agar, and MacConkey agar for isolation and identification of the contaminating organism. All TSB tubes (regardless of turbidity) are further checked for growth on solid media. This is done by plating aliquots of 0.05 ml from each TSB tube onto chocolate agar and incubating for 72 hours in the same atmosphere as the broths.

Maintenance of *Chlamydia trachomatis*: Type E (Seattle strain) is used for testing of the subject media. A volume (less than 50 microliters) of frozen Type E is added to a transport medium tube such that the inclusion forming units are approximately 2500 per ml. The inoculated tube is stored at 2° C. to 8° C. for 24 hours. An inoculum of 250 microliters from the stored tube should result in a positive culture with 200 to 400 inclusion forming units when cultured in McCory or BGMK cells. Results are recorded as Chlamydia maintained or Chlamydia not maintained. Any lots which do not maintain Chlamydia will be rejected.

Maintenance of Mycoplasma/Ureaplasma: *M. pneumoniae*, *M. hominis*, and *U. urealyticum* are used for testing of the subject transport media. The organisms are grown to a simulated patient specimen titer and are inoculated into the media. They are stored at 2° C. to 8° C. for 48 hours and are re-inoculated into plates to determine growth and viability. The results are recorded as Mycoplasma/Ureaplasma maintained or not maintained. Any lots which do not maintain these organisms will be rejected.

EXAMPLE 2

Percent Recovery of a Variety of Agents From Transport Medium C

The recovery rates following storage in Transport Medium C of various microbial agents are shown in Table 2 below. Vials containing transport Medium C were inoculated with viral (respiratory syncitial virus, herpes simplex 1, cytomegalovirus, and influenza) and non-viral test organisms (Chlamydia, Mycoplasma, and Ureaplasma) and stored at 2°–8° C. The samples were tested at 8 hours, 24 hours, and 48 hours. Each of the tested microbial agents was successfully recovered from the vials after 48 hours showing Transport Medium C supports microbial viability of these fastidious pathogens during storage at refrigeration temperatures.

TABLE 2

Recovery Percentages of Various Agents

| Microbe Name/Time | 8 Hours | 24 Hours | 48 Hours |
| --- | --- | --- | --- |
| respiratory syncitial virus | 75% | 64% | 58% |
| herpes simplex type 1, McIntyre | | 88% | 49% |
| cytomegalovirus (AD 169) | | 58% | 27% |
| influenza A H3N2, Shanghai 87 | | 87% | 74% |
| *Chlamydia trachomatis* | 82% | 43% | 33% |
| *Mycoplasma pneumoniae* | | Recovered | Recovered |
| *Mycoplasma hominis* | | Recovered | Recovered |
| *Ureaplasma urealyticum* | | Recovered | Recovered |

EXAMPLE 3

Comparisons of Transport Media for the Recovery of Various Agents

The subject transport medium was compared to other transport media for its ability to sustain viability of certain fastidious viral, mycoplasmal, and ureaplasmal pathogens over a one-week period of time and under different temperature conditions. For example, the storage of various pathogens in the subject medium versus Bartels Viral Transport Medium (VTM) (Baxter, Chicago, Ill.) is known for the viruses influenza A H3N2, respiratory syncitial virus (RSV), cytomegalovirus (CMV) and herpes simplex type 1, McIntyre, in Tables 3, 4, 5, and 6, respectively. Samples were compared at 25° C. and 2° C. Viral agents were stored in the transport media for up to one week. Recovery of most viral agents from Transport Medium after one week were markedly superior than corresponding media where samples were held at 25° C.

TABLE 3

Transport Media Comparison, influenza A H3N2
(19,250 ff at time zero)

| | 24 Hours | 48 Hours | 72 Hours | 96 Hours | 1 Week |
|---|---|---|---|---|---|
| 25° C. | | | | | |
| Transport Medium C | 15280 | 8965 | 5610 | 3135 | 605 |
| Bartels VTM | 14685 | 9295 | 5500 | 3080 | 460 |
| 2° C. | | | | | |
| Transport Medium C | 16885 | 14300 | 12210 | 10615 | 6875 |
| Bartels VTM | 16610 | 14575 | 11990 | 10725 | 6600 |

VTM = Viral Transport Medium

TABLE 4

Transport Media Comparison, RSV
(2255 × 55 ff at time zero)

| | 8 Hours | 24 Hours | 48 Hours | 72 Hours | 1 Week |
|---|---|---|---|---|---|
| 25° C. | | | | | |
| Transport Medium C | 1925 | 1760 | 1210 | 935 | 475 |
| Bartels VTM | 1375 | 990 | 660 | 490 | 58 |
| 2° C. | | | | | |
| Transport Medium C | 1705 | 1455 | 1320 | 1205 | 330 |
| Bartels VTM | 1375 | 1155 | 1045 | 630 | 275 |

TABLE 5

Transport Media Comparison, CMV Strain AD 169
(20,460 ff at time zero)

| | 24 Hours | 48 Hours | 72 Hours | 96 Hours | 1 Week |
|---|---|---|---|---|---|
| 25° C. | | | | | |
| Transport Medium C | 9295 | 6655 | 5335 | 3960 | 287 |
| Bartels VTM | 11440 | 8030 | 5390 | 4510 | 301 |
| 2° C. | | | | | |
| Transport Medium C | 11880 | 5555 | 2585 | 1760 | 1430 |
| Bartels VTM | 11605 | 6435 | 2530 | 1760 | 1045 |

TABLE 6

Transport Media Comparison, herpes simplex type I McIntyre-
A549 (40,865 × 55 infectious particles at time zero)

| | 24 Hours | 48 Hours | 72 Hours | 96 Hours | 1 Week |
|---|---|---|---|---|---|
| 25° C. | | | | | |
| Transport Medium C | 26950 | 12265 | 3520 | 2530 | 475 |
| Bartels VTM | 28050 | 7810 | 3575 | 495 | 183 |

TABLE 6-continued

Transport Media Comparison, herpes simplex type I McIntyre-
A549 (40,865 × 55 infectious particles at time zero)

| | 24 Hours | 48 Hours | 72 Hours | 96 Hours | 1 Week |
|---|---|---|---|---|---|
| 2° C. | | | | | |
| Transport Medium C | 36025 | 19965 | 12980 | 8910 | 4895 |
| Bartels VTM | 36850 | 19030 | 13035 | 9295 | 3905 |

In addition, the subject medium was compared to both MSP and Bartels CTM for storage of Chlamydia samples (Table 7). In this comparison, the inoculum was 9700 IFU at time zero.

As clearly shown in Table 7, the subject transport medium demonstrated far greater recovery rates than samples stored in the other media. For example, Chlamydia samples kept at 2° C. supported Chlamydia viability for up to 72 hours in Transport Medium B whereas, using the other media, no Chlamydia was recovered after only 24 hours of storage.

TABLE 7

Transport Media Comparison Chlamydia - Type E - Seattle Strain

| | 8 Hours | 24 Hours | 48 Hours | 72 Hours |
|---|---|---|---|---|
| 25° C. | | | | |
| Transport Medium C | 3500 | 1220 | 188 | 106 |
| MSP | 2600 | 100 | 0 | 0 |
| Bartels CTM | 1600 | 256 | 0 | 0 |
| 2° C. | | | | |
| Transport Medium C | 7920 | 4180 | 3240 | 2260 |
| MSP | 5520 | 3460 | 2680 | 1360 |
| Bartels CTM | 5580 | 3100 | 500 | 480 |

EXAMPLE 4

Freeze-Thaw Properties of Transport Medium C

In one study, 33 positive clinical specimens of varicella-zoster virus (VZV) were identified from a batch of 102 patient samples. VZV is an extremely labile virus under cryopreservation. All samples had been frozen in Transport Medium C for a period of one year, at −70° C. Two additional positive specimens were identified from a different batch of 44 samples which had originally been identified as negative specimens.

EXAMPLE 5

Use of Transport Medium C in a Commercial PCR Assay for *Chlamydia trachomatis* (*Ct.*)

The effectiveness of Transport Medium C as compared to Amplicor transport medium (Roche Diagnostics, Nutley, N.J.) for use in the Ct PCR assay (Roche).

A) Two female cervical swabs were collected from each participant randomly selected from a high prevalence population. The first swab was placed in Transport Medium C. The second was swirled in the Amplicor and discarded as per the manufacturer's instructions.

One ml of the vortexed Transport Medium C and Amplicor were each mixed with 1.0 ml of Specimen Diluent (Roche) and incubated for 10 minutes at room temperature. Then, 50 μl of each prepared sample was used for PCR amplification according to the manufacturer's instructions.

B) The second group of samples were those received routinely in Transport Medium C for testing, i.e., a low prevalence group. A group of 100 negatives and 25 true positives were analyzed by PCR. After vortexing, a 1.0 ml aliquot was removed from the Transport Medium C and placed in the Amplicor transport media. One ml of the Amplicor/Transport Medium C mix and of the Transport Medium C alone were then mixed with Specimen Diluent and assayed as above.

All specimens were tested by multiple methods: culture, EIA (Syva, Palo Alto, Calif.), SFA (Syva, Palo Alto, Calif.), or DNA probe (GenProbe, San Diego, Calif.). True positives were those determined to be positive by culture, or by at least two nonculture methods.

C) Results. Among 30 samples from the high prevalence population there were 10 true positives. Nine were positive by PCR and culture, or by two or more of the antigen/probe methods. One was positive by PCR alone (both the Transport Medium C and Amplicor Media). One Amplicor PCR positive specimen was negative with the Transport Medium C PCR test.

In the low prevalence group, both Amplicor and Transport Medium C detected 19 of the 25 true positives. Transport Medium C detected 5 positives which were missed by Amplicor (perhaps due to dilution), and both missed 1 positive. One additional PCR positive specimen was detected in both transports from the 100 negatives. Thus, it can be concluded that Transport Medium C can be used directly with Specimen Diluent in this PCR assay without significant reduction in true positives or increase in false positives. Specimens received in Transport Medium C which are then placed in Amplicor medium prior to mixing with the Specimen Diluent may show false negatives due to dilution or other factors.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Amies (1967) *Can. J. Public Health* 58: 296–300.
Bailey et al. (1978) "Specimen Containers and their Transport," *Diagnostic Microbiology* 29–32, The C. V. Mosby Co., St. Louis, Mo.
Bowie and Holmes (1977) in *Infectious Diseases*, 2 ed., (Hoeprich, Paul D., ed.) Harper & Row, Hagerstown, pp. 486–487.
Saikki, R. K. (1989) in *PCR Technology*, Stockton Press, United Kingdom, pp. 7–16.
Stuart et al. (1954) *Can. J. Public Health*, 45: 73–83.

I claim:

1. An aqueous microbial transport medium capable of maintaining viability of a plurality of microorganisms selected from the group consisting of Chlamydia, Mycoplasma, Ureaplasma, and viruses, said medium having physiological pH and consisting essentially of:

| | |
|---|---|
| $H_2O$ | 24.89 liters |
| sucrose | 1711.43 g |
| HEPES | 148.99 g |
| KCl | 10.0 g |
| L-glutamic acid | 18.0 g |
| phenol red | 13.0 ml |
| NaOH | 36.0 ml |
| $CaCl_2$ | 6.63 g |
| $MgSO_4 \cdot 7H_2O$ | 5.0 g |
| BSA | 250 g |
| vancomycin | 0.62 g |
| colistin | 0.35 g |
| amphotericin | 60.0 ml |

2. An aqueous microbial transport medium having physiological pH and consisting essentially of:

| | |
|---|---|
| $H_2O$ | 24.89 liters |
| sucrose | 1711.43 g |
| HEPES | 148.99 g |
| KCl | 10.0 g |
| L-glutamic acid | 18.0 g |
| phenol red | 13.0 ml |
| NaOH | 36.0 ml |
| $CaCl_2$ | 6.63 g |
| $MgSO_4 \cdot 7H_2O$ | 5.0 g |
| BSA | 125 g |
| gelatin | 125 g |
| vancomycin | 0.62 g |
| colistin | 0.35 g |
| amphotericin | 60.0 ml |

* * * * *

UNITED STATES PATENT AND TRADEMARK OFFICE
CERTIFICATE OF CORRECTION

PATENT NO. : 5,545,555

DATED : August 13, 1996

INVENTOR(S) : Stephen G. Racioppi; James P. Brinker

It is certified that error appears in the above-indentified patent and that said Letters Patent is hereby corrected as shown below:

Column 2: Line 60: "patbogen" should read --pathogen--; Line 61: "patbogen" should read --pathogen--; Line 63: "patbogen" should read --pathogen--.

Column 3: Line 16: "vital" should read --viral--.

Column 6: Line 36: "vital" should read --viral--.

Signed and Sealed this

Twelfth Day of November, 1996

Attest:

BRUCE LEHMAN

Attesting Officer   Commissioner of Patents and Trademarks